US010080367B2

(12) United States Patent
Saito et al.

(10) Patent No.: US 10,080,367 B2
(45) Date of Patent: Sep. 25, 2018

(54) ACIDIC ELECTROLYZED WATER AND PRODUCTION METHOD THEREFOR

(71) Applicant: Molex, LLC, Lisle, IL (US)

(72) Inventors: Kazusa Saito, Yamato (JP); Kousuke Taketomi, Yamato (JP); Megumi Muramoto, Yamato (JP); Atsuhito Horino, Ebina (JP)

(73) Assignee: Molex, LLC, Lisle, IL (US)

( * ) Notice: Subject to any disclaimer, the term of this patent is extended or adjusted under 35 U.S.C. 154(b) by 0 days.

(21) Appl. No.: 15/433,122

(22) Filed: Feb. 15, 2017

(65) Prior Publication Data
US 2017/0156341 A1 Jun. 8, 2017

Related U.S. Application Data

(62) Division of application No. 14/411,566, filed as application No. PCT/IB2013/002588 on Jun. 28, 2013, now abandoned.

(30) Foreign Application Priority Data

Jun. 28, 2012 (JP) .................................. 2012-145990
Jun. 21, 2013 (JP) .................................. 2013-131044

(51) Int. Cl.
A61K 31/74 (2006.01)
A61K 33/40 (2006.01)
A61K 33/14 (2006.01)
A01N 59/26 (2006.01)
C02F 1/467 (2006.01)
A01N 59/00 (2006.01)
A61K 8/20 (2006.01)
A61K 8/24 (2006.01)
A61Q 11/00 (2006.01)
A61Q 11/02 (2006.01)
C25B 1/26 (2006.01)
A61Q 19/10 (2006.01)
A61Q 17/00 (2006.01)
C02F 1/66 (2006.01)
C02F 103/02 (2006.01)
C02F 103/04 (2006.01)
C02F 1/461 (2006.01)

(52) U.S. Cl.
CPC ............. *A01N 59/26* (2013.01); *A01N 59/00* (2013.01); *A61K 8/20* (2013.01); *A61K 8/24* (2013.01); *A61Q 11/00* (2013.01); *A61Q 11/02* (2013.01); *A61Q 17/005* (2013.01); *A61Q 19/10* (2013.01); *C02F 1/4674* (2013.01); *C25B 1/26* (2013.01); *A61K 2800/83* (2013.01); *A61K 2800/92* (2013.01); *C02F 1/66* (2013.01); *C02F 2001/46185* (2013.01); *C02F 2103/026* (2013.01); *C02F 2103/04* (2013.01); *C02F 2201/461* (2013.01); *C02F 2305/023* (2013.01)

(58) Field of Classification Search
IPC ............... A61K 8/72,33/40, 33/14, 8/73; C24B 15/00
See application file for complete search history.

(56) References Cited

U.S. PATENT DOCUMENTS

| 3,481,857 | A | 12/1969 | Gray |
| 4,176,022 | A | 11/1979 | Darlington |
| 4,954,316 | A | 9/1990 | Globus |
| 5,695,746 | A | 12/1997 | Garlick, Jr. et al. |
| 5,820,854 | A * | 10/1998 | Glandorf .................. A61K 8/19 424/49 |
| 5,858,201 | A | 1/1999 | Otsuka et al. |
| 6,200,529 | B1 | 3/2001 | Riggs, Jr. |
| 6,426,066 | B1 | 7/2002 | Najafi et al. |
| 2005/0074421 | A1 | 4/2005 | Tanaka |
| 2008/0169202 | A1 | 7/2008 | Bargeman et al. |
| 2011/0168567 | A1 | 7/2011 | Smith et al. |
| 2013/0330116 | A1 | 12/2013 | Mello et al. |

FOREIGN PATENT DOCUMENTS

| JP | 09-108681 A | 4/1997 |
| JP | 2000-247808 | 9/2000 |
| JP | 2001-271098 A | 10/2001 |
| JP | 2004-130265 A | 4/2004 |
| JP | 2009-136814 | 6/2009 |
| TW | 200902453 A | 1/2009 |
| WO | WO 2006-008877 A1 | 1/2006 |

* cited by examiner

Primary Examiner — Walter E Webb
(74) Attorney, Agent, or Firm — James A. O'Malley

(57) ABSTRACT

To provide acidic electrolyzed water having disinfecting power for a long period of time (for example, six months or more), and a production method for this acidic electrolyzed water. The acidic electrolyzed water has an effective chlorine concentration equal to or greater than 15 ppm, and contains an acid salt of an inorganic acid.

10 Claims, 5 Drawing Sheets

FIG. 3A
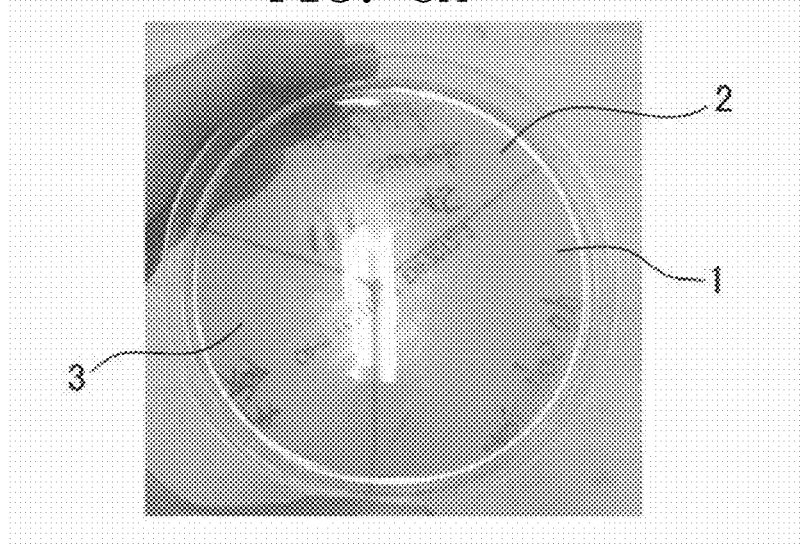
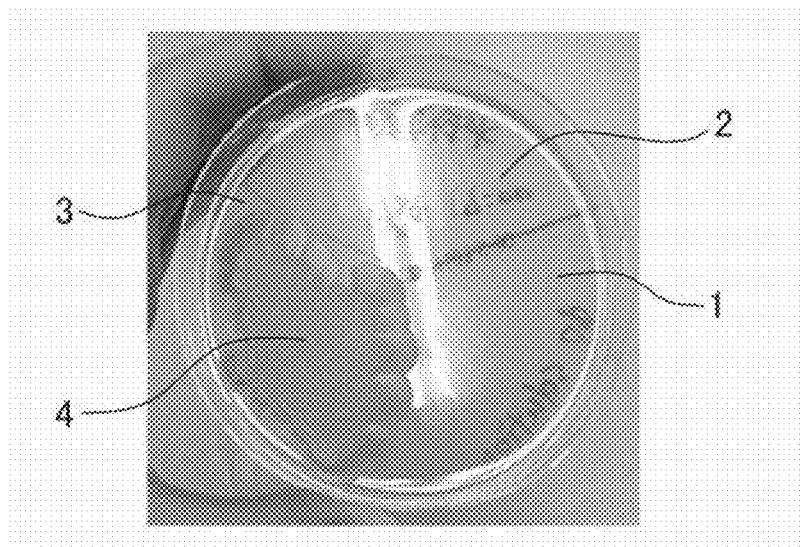
FIG. 3B

ACIDIC ELECTROLYZED WATER AND PRODUCTION METHOD THEREFOR

REFERENCE TO RELATED APPLICATIONS

The Present Disclosure is a divisional of U.S. patent application Ser. No. 14/411,566, which claims priority to PCT Application No. PCT/IB2013/002588, filed on Jun. 28, 2013, which in turns claims priority to prior-filed Japanese Patent Application Nos. 2012-145990, entitled "Acidic Electrolyzed Water and Production Method Therefor," filed on Jun. 28, 2012 with the Japanese Patent Office (JPO); and 2013-131044, also entitled "Acidic Electrolyzed Water and Production Method Therefor," filed on Jun. 21, 2013 also with the JPO. The content of each of the aforementioned Patent Applications are incorporated in their entireties herein.

BACKGROUND OF THE PRESENT DISCLOSURE

The Present Disclosure relates, generally, to acidic electrolyzed water and a production method for acidic electrolyzed water.

Acidic electrolyzed water is electrolyzed water obtained by electrolysis of a solution of water and an electrolyte such as sodium chloride or hydrochloric acid. Acidic electrolyzed water with a pH value of 2.7 or less is known as "highly acidic water," and has a strong disinfecting action. An example of highly acidic water is illustrated in PCT Patent Application No. PCT/JP1995/0001503, the content of which is hereby incorporated herein in its entirety.

However, highly acidic water has a short disinfecting power retention period, and this makes long-term storage difficult.

SUMMARY OF THE PRESENT DISCLOSURE

The Present Disclosure provides acidic electrolyzed water having disinfecting power for a long period of time (at least three weeks or more, for example, six months or more), and a production method for this acidic electrolyzed water.

One aspect of the Present Disclosure is acidic electrolyzed water having an effective chlorine concentration equal to or greater than 15 ppm, and containing an acid salt of an inorganic acid. In the Present Disclosure, "acid salt" is a salt containing hydrogen atoms that can be substituted by metal atoms. Acid salt also refers to a salt which dissolves in water and has acidic properties (a pH value of less than 7.0). Preferably, the pH value of the acidic electrolyzed water is equal to or greater than 3.0 and less than 7.0. Preferably, the LD50 value of the acid salt of the inorganic acid in the acidic electrolyzed water is greater than 300 mg. In the acidic electrolyzed water, the acid salt of the inorganic acid is at least one selected from among disodium dihydrogen pyrophosphate, sodium hexametaphosphate, and sodium dihydrogen phosphate.

Another aspect of the Present Disclosure is a production method for acidic electrolyzed water which includes the step of adding an acid salt of an inorganic acid to an acidic electrolyzed water base material having an effective chlorine concentration equal to or greater than 15 ppm. This also includes the step of purifying the acidic electrolyzed water base by electrolyzing a chlorine-based electrolyte solution.

Another aspect of the Present Disclosure is a cleanser containing this acidic electrolyzed water.

Another aspect of the Present Disclosure is a denture cleanser containing this acidic electrolyzed water.

Another aspect of the Present Disclosure is a disinfectant containing this acidic electrolyzed water.

Because this acidic electrolyzed water has an effective chlorine concentration equal to or greater than 15 ppm, and contains an acid salt of an inorganic acid, it has disinfecting power for a long period of time (at least three weeks or more, for example, six months or more). This makes long-term storage possible. It also makes storage easy because it retains its disinfecting power even when it is not stored in a dark place, as long as direct sunlight is avoided.

BRIEF DESCRIPTION OF THE FIGURES

The organization and manner of the structure and operation of the Present Disclosure, together with further objects and advantages thereof, may best be understood by reference to the following Detailed Description, taken in connection with the accompanying Figures, wherein like reference numerals identify like elements, and in which:

FIG. 3A is a photograph showing the disinfecting power evaluation results of the acidic electrolyzed water containing disodium dihydrogen pyrophosphate was used as the acid salt of an inorganic acid in the first example of the Present Disclosure (at the start of the test);

FIG. 3B is a photograph showing the disinfecting power evaluation results of the acidic electrolyzed water containing disodium dihydrogen pyrophosphate as the acid salt of an inorganic acid in the first example of the Present Disclosure when used immediately after preparation (after cultivation for 24 hours);

DESCRIPTION OF THE PREFERRED EMBODIMENTS

Figure 1:
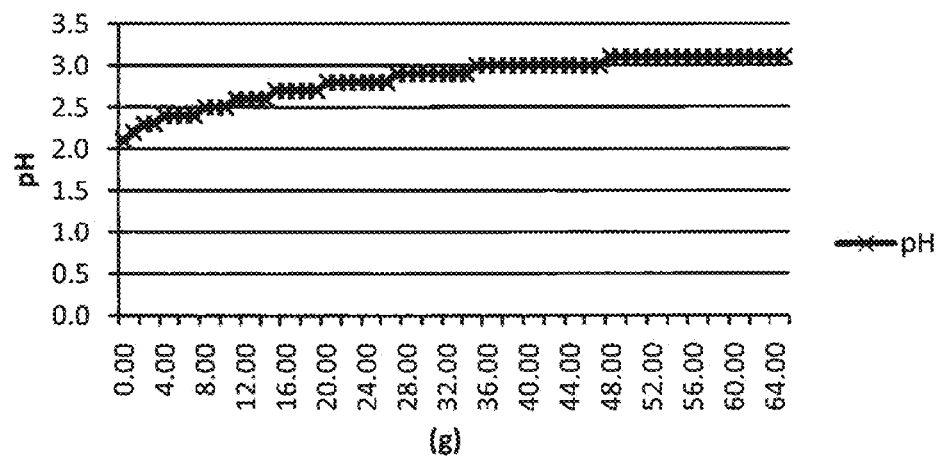
FIG. 1 is a graph showing the relationship between the pH value and the amount of disodium dihydrogen pyrophosphate when acidic electrolyzed water with a pH value of 2.1 was used as the base material and disodium dihydrogen pyrophosphate was used as the acid salt of an inorganic acid in the first example of the Present Disclosure.

While the Present Disclosure may be susceptible to embodiment in different forms, there is shown in the Figures, and will be described herein in detail, specific embodiments, with the understanding that the Present Disclosure is to be considered an exemplification of the principles of the Present Disclosure, and is not intended to limit the Present Disclosure to that as illustrated.

As such, references to a feature or aspect are intended to describe a feature or aspect of an example of the Present Disclosure, not to imply that every embodiment thereof must have the described feature or aspect. Furthermore, it should be noted that the description illustrates a number of features. While certain features have been combined together to illustrate potential system designs, those features may also be used in other combinations not expressly disclosed. Thus, the depicted combinations are not intended to be limiting, unless otherwise noted.

In the embodiments illustrated in the Figures, representations of directions such as up, down, left, right, front and rear, used for explaining the structure and movement of the various elements of the Present Disclosure, are not absolute, but relative. These representations are appropriate when the elements are in the position shown in the Figures. If the description of the position of the elements changes, however, these representations are to be changed accordingly. Further, in the Present Disclosure, "parts" refers to "parts by mass" unless otherwise indicated.

1. Acidic Electrolyzed Water

1.1. Acid Salts of Inorganic Acid

The acidic electrolyzed water in the present embodiment of the Present Disclosure includes an acid salt of an inorganic acid. The acidic electrolyzed water in the Present Disclosure can maintain disinfecting power for a long period of time (at least three weeks or more, for example, six months or more). When the acid salt of the inorganic acid is dissolved in water, the solution is acidic (having a pH value of less than 7.0), and the amount of acid salt of the inorganic acid in the acidic electrolyzed water of the present embodiment has very little effect on control of the pH value. As a result, it is easy to control the pH value when the acidic electrolyzed water in the present embodiment is prepared.

Preferably, from the standpoint of low toxicity, the acid salt of the inorganic acid has an LD50 value greater than 300 mg. The use of an acid salt of an inorganic acid with such an LD50 value is preferred from the standpoint of low toxicity when the acidic electrolyzed water of the present embodiment is used in an application as a medical, food or cosmetic product.

The acid salt of an inorganic acid may be a sodium salt, potassium salt, magnesium salt, or barium salt. However, a sodium salt is preferred from the standpoint of safety. Because the acidic electrolyzed water of the preferred embodiment is easier to adjust to a predetermined pH value (for example, a pH value equal to or greater than 3.0 and less than 7.0), an acid salt of an inorganic acid that is weakly acidic is preferred. The acidic electrolyzed water in the present embodiment has a pH value equal to or greater than 3.0 and less than 7.0. More specifically, the acid salt of the inorganic acid may be at least one selected from among disodium dihydrogen pyrophosphate, sodium hexametaphosphate, and sodium dihydrogen phosphate. One or more type of acid salt of an inorganic acid may be added.

The amount of acid salt of an inorganic acid added may be 16 g/L or more in the case of disodium dihydrogen pyrophosphate, 1.4 g/L or more in the case of sodium hexametaphosphate, and 4.4 g/L or more in the case of sodium dihydrogen phosphate.

For example, when the acidic electrolyzed water of the preferred embodiment is incorporated into a dental cleanser such as a denture cleanser or mouthwash, the acid salt of an inorganic acid is preferably disodium dihydrogen pyrophosphate because it can prevent the re-deposition of tartar. The amount of disodium dihydrogen pyrophosphate in the acidic electrolyzed water of the present embodiment is preferably 16 g/L or more because it can both maintain disinfectant power for a long period of time (at least three weeks or more, for example, six months or more), and prevent the re-deposition of tartar. The acidic electrolyzed water of the present embodiment may also include components other than an acid salt of an inorganic acid as long as the amount added does not adversely affect the properties of the acidic electrolyzed water of the present embodiment.

For example, when the acidic electrolyzed water of the preferred embodiment is incorporated into a medical, food or cosmetic product, the acid salt of an inorganic acid is preferably sodium hexametaphosphate because it has a moisturizing action. The amount of disodium dihydrogen pyrophosphate in the acidic electrolyzed water of the present embodiment is preferably 1.4 g/L or more.

1.2. Effective Chlorine Concentration

The acidic electrolyzed water of the present embodiment has an effective chlorine concentration equal to or greater than 15 ppm, preferably equal to or greater than 20 ppm. In the Present Disclosure, the effective chlorine concentration of the acidic electrolyzed water can be measured using a commercially available residual chlorine concentration measuring device.

1.3. pH Value

The pH value of the acidic electrolyzed water of the present embodiment is preferably equal to or greater than 3.0 and less than 7.0 from the standpoint of exhibiting disinfecting power, ensuring the stability of the acidic electrolyzed water, and suppressing the occurrence of trihalomethane. In the Present Disclosure, the pH value of the acidic electrolyzed water can be measured using a commercially available pH measuring device.

1.4. Chloride Ion Concentration

Preferably, the acidic electrolyzed water of the present embodiment has hardly any chloride ions derived from the electrolyte because this suppresses metal corrosion.

1.5. Operation and Effects

Because the acidic electrolyzed water of the present embodiment has an effective chlorine concentration equal to or greater than 15 ppm, and contains an acid salt of an inorganic acid, it has disinfecting power for a long period of time (at least three weeks or more, for example, six months or more). This makes long-term storage possible. It also makes storage easy because it retains its disinfecting power even when it is not stored in a dark place, as long as direct sunlight is avoided.

Figure 5:
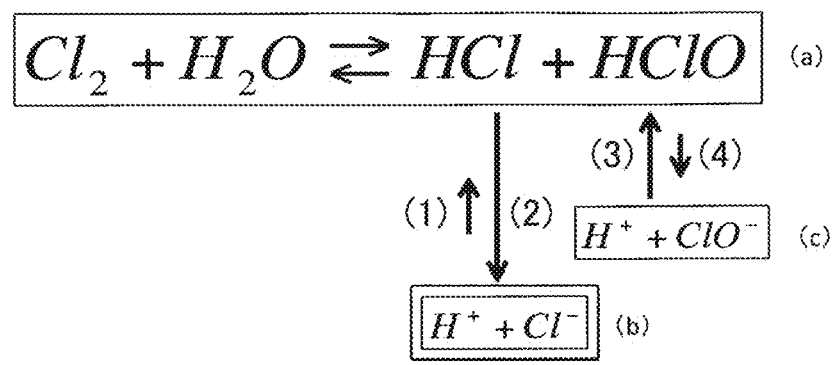
FIG. 5 shows the chemical equilibrium equation in the acidic electrolyzed water of the Present Disclosure.

FIG. 5 shows the chemical equilibrium equation in the acidic electrolyzed water of the Present Disclosure. Equation (a) in FIG. 5 maintains the equilibrium in the acidic electrolyzed water of the Present Disclosure. Hydrochloric acid (HCl) maintains the equilibrium between Equation (a) of FIG. 5 and Equation (b) of FIG. 5 as indicated by arrows (1) and (2), and hypochlorous acid (HClO) maintains the equilibrium between Equation (a) of FIG. 5 and Equation (c) of FIG. 5 as indicated by arrows (3) and (4). Because hydrochloric acid is a very strong acid, ionization readily occurs and arrow (2) predominates. Because hypochlorous acid is affected by the hydrochloric acid, hardly any ionization occurs and arrow (3) predominates.

Because the acidic electrolyzed water of the present embodiment includes an acid salt of an inorganic acid, the acid salt of the inorganic acid is dissolved in the acidic electrolyzed water of the present embodiment, anions derived from the acid salt of the inorganic salt bond with the hydrogen ions and reduce the number of free hydrogen atoms, and the pH value rises. Because this biases the equilibrium in Equation (a) of FIG. 5 to the right, the release of chlorine gas from the acidic electrolyzed water can be suppressed. It can also retain disinfecting power over a long period of time.

When an organic material such as an organic acid or salt of an organic acid is present in the acidic electrolyzed water, the organic material is oxidized by the chlorine, and the chlorine is consumed. As a result, the disinfecting power may decline. However, because the acid salt of an inorganic acid in the present embodiment is not an organic material, it is not oxidized by chlorine, and the disinfecting power is maintained for a long period of time. More specifically, the oxidizing power can be maintained for a long period of time when the acidic electrolyzed water of the present embodiment is substantially free of organic materials.

2. Acidic Electrolyzed Water Production Method

Another aspect of the Present Disclosure is a production method for acidic electrolyzed water which includes the addition of an acid salt of an inorganic acid to an acidic electrolyzed water base material having an effective chlorine concentration equal to or greater than 15 ppm.

The acidic electrolyzed water base material used as the base material in the production method for the acidic electrolyzed water of the present embodiment (referred to below as the "acidic electrolyzed water base material") has an effective chlorine concentration equal to or greater than 15 ppm (preferably equal to or greater than 20 ppm).

2.1 Preparation of Acidic Electrolyzed Water Base Material

The production method for acidic electrolyzed water in the present embodiment can include a step in which the acidic electrolyzed water base material is purified by electrolyzing a chlorine-based electrolyte solution.

In the Present Disclosure, a "chlorine-based electrolyte" is an electrolyte that produces chlorine ions when dissolved in water. Examples of chlorine-based electrolytes include chlorides of alkali metals (such as sodium chloride and potassium chloride) and chlorides of alkaline-earth metals (such as calcium chloride or magnesium chloride).

The electrolyzed water base material can be purified using a water electrolyzing device in which a cathode chamber and an anode chamber are partitioned by a membrane (two-tank water electrolyzing device). Here, the cathode chamber and the anode chamber are filled with chlorine-based electrolyte solution and electrolysis is performed. The electrolyzed water base material can also be purified using a water electrolyzing device in which a cathode chamber and an anode chamber are partitioned by a membrane, and in which a middle chamber is partitioned from both the cathode chamber and an anode chamber by two membranes (three-tank water electrolyzing device). Here, the cathode chamber and the anode chamber are filled with a highly concentrated chlorine-based electrolyte solution and electrolysis is performed.

When the water electrolysis is performed using a two-tank water electrolyzing device, the concentration of the chlorine-based electrolyte solution is preferably from 0.1 to 0.2%. When the water electrolysis is performed using a three-tank water electrolyzing device, the concentration of the chlorine-based electrolyte solution does not have a significant effect on the properties of the prepared acidic electrolyte water base material, but should be as high as possible.

From the standpoint of a low concentration of electrolytes in the acidic electrolyzed water base material, the acidic electrolyzed water base material should be prepared using a three-tank water electrolyzing device. When the acidic electrolyzed water base material is prepared using a two-tank water electrolyzing device, the concentration of the electrolytes in the acidic electrolyzed water base material can be lowered by adding purified water (distilled water or ion-exchanged water) to the electrolyzed water used in the two-tank water electrolyzing device.

The acidic electrolyzed water base material may be prepared using one of the water electrolyzing devices described above. Alternatively, since there are several commercially available water electrolyzing devices, the acidic electrolyzed water base material may be prepared using one of these commercially available water electrolyzing devices.

Examples of commercially available water electrolyzing devices include the Excel FX™ (model: MX-99, manufacturer: Nambu Co., Ltd.); ROX-10WB3 (manufacturer: Hoshizaki Denki Co., Ltd.); a-Light (manufacturer: Amano Co., Ltd.); ESS-ZERO™ (manufacturer: Shinsei Co., Ltd.); and FINEOXER Desktop FO-1000S2™ (manufacturer: First Ocean Co., Ltd.). The acidic electrolyzed water base material can be prepared using any one of these commercially available water electrolyzing devices. The acidic electrolyzed water base material can also be produced using the electrolyzed water production method described in Japanese Patent Application No. 2000-108971, the content of which is hereby incorporated herein in its entirety.

2.2 Addition of Acid Salt of Inorganic Acid to Acidic Electrolyzed Water Base Material The amount of acid salt of an inorganic acid added to the acidic electrolyzed water base material when the acidic electrolyzed water of the present embodiment is produced is that which was described in Section 1.1. Acid Salts of Inorganic Acid.

Also, the pH value of the acidic electrolyzed water base material during the production of the acidic electrolyzed water of the present embodiment is preferably equal to or greater than 1.7 and less than 7.0, more preferably equal to or greater than 1.7 and less than 6.0, and even more preferably equal to or greater than 1.8 and less than 6.0.

3. Applications

The acidic electrolyzed water of the present embodiment can be used as a disinfectant and/or cleanser for disinfecting and/or cleaning operations in various industries, such as the medical industry, the livestock industry, the food processing industry, and manufacturing. For example, it can be used to disinfect and/or clean tools or wounds in medicine or animal husbandry.

The acidic electrolyzed water of the present embodiment can also be used as an oral cleanser (toothpaste, mouthwash, dental paste) or a denture cleanser. For example, when the acidic electrolyzed water of the preferred embodiment contains disodium dihydrogen pyrophosphate, it is suitable for use as a denture cleanser because it can prevent the re-deposition of tartar. When the acidic electrolyzed water of the preferred embodiment contains sodium hexametaphosphate, it is suitable for use as a lotion, disinfectant spray, antiseptic or hand disinfectant because of its moisturizing action.

Because the acidic electrolyzed water in the present embodiment is highly stable, acidic electrolyzed water can be placed in a container.

4. Example

The following is a more detailed explanation of the Present Disclosure with reference to an example, but the Present Disclosure is not restricted to this example.

4.1. Example 1

4.1.1. Preparation Example 1 (Preparation of Acidic Electrolyzed Water Base Material)

First, acidic electrolyzed water base materials 1 and 2 were prepared for use in the example. Acidic electrolyzed water base materials 1 and 2 were produced using acidic electrolyzed water production equipment (trade name: Fineoxer FO-1000S2 Desktop Model). When acidic electrolyzed water base materials 1 and 2 were prepared sodium chloride was used as the chlorine-based electrolyte. Acidic electrolyzed water base material 1 had an effective chlorine concentration of 91 ppm, and a pH value of 2.1. Acidic electrolyzed water base material 2 had an effective chlorine concentration of 91 ppm, and a pH value of 1.7.

In this example, the pH value was measured using a pH measuring device (trade name: Digital pH Pentester from SAGA Electronic Enterprise Co., Ltd.), and the effective chlorine concentration was measured using a chlorine concentration measuring device (trade name: Aquab from Shibata Chemical Co., Ltd.).

4.1.2. Preparation Example 2 (Preparation of Acidic Electrolyzed Water Containing Acid Salt of Inorganic Acid)

Next, disodium dihydrogen pyrophosphate (Taihei Chemical Industrial Co., Ltd.) was added and dissolved in acidic electrolyzed water base material 1 to prepare acidic electrolyzed water containing disodium dihydrogen pyrophosphate. Here, the pH value of the acidic electrolyzed water was measured each time the added amount of disodium dihydrogen pyrophosphate was changed. FIG. 1 is a graph showing the relationship between the pH value and the added amount of disodium dihydrogen pyrophosphate. FIG. 1 indicates the added amount (g) of disodium dihydrogen pyrophosphate per liter of acidic electrolyzed water base material.

It is clear from FIG. 1 that more than 16 g of disodium dihydrogen pyrophosphate had to be added to raise the pH value of the acidic electrolyzed water to 2.7 or more when the pH value of the acidic electrolyzed water base material was 2.1.

Also, 20 g/L disodium dihydrogen pyrophosphate was added and dissolved in acidic electrolyzed water base material 1 to prepare the acidic electrolyzed water, which was stored for six months at room temperature (26° C.) without shielding the preparation from light. After storage for six months at room temperature, the effective chlorine concentration was 49 ppm, and the pH value was 3.1. It was clear that the effective chlorine concentration, pH value and chlorine ion concentration remained unchanged, even when the acidic electrolyzed water containing an acid salt of an inorganic acid (disodium dihydrogen pyrophosphate) was stored for a long period of time.

4.1.3. Preparation Example 3 (Preparation of Acidic Electrolyzed Water Containing Acid Salt of Inorganic Acid)

Figure 2:
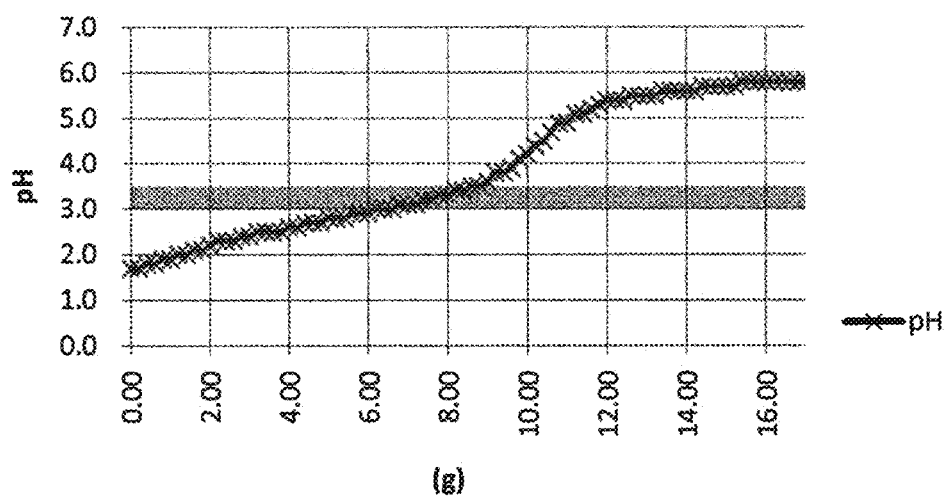
FIG. 2 is a graph showing the relationship between the pH value and the amount of sodium hexametaphosphate when acidic electrolyzed water with a pH value of 1.7 was used as the base material and sodium hexametaphosphate was used as the acid salt of an inorganic acid in the first example of the Present Disclosure.

Next, sodium hexametaphosphate (Happou Shokai Co., Ltd.) was added and dissolved in acidic electrolyzed water base material 1 to prepare acidic electrolyzed water containing sodium hexametaphosphate. Here, the pH value of the acidic electrolyzed water was measured each time the added amount of sodium hexametaphosphate was changed. FIG. 2 is a graph showing the relationship between the pH value and the added amount of sodium hexametaphosphate. FIG. 2 indicates the added amount (g) of sodium hexametaphosphate per liter of acidic electrolyzed water base material.

It is clear from FIG. 2 that more than 6.2 g of sodium hexametaphosphate had to be added to raise the pH value of the acidic electrolyzed water to 3.0 or more when the pH value of the acidic electrolyzed water base material was 1.7.

4.1.4. Test Example 1 (Disinfecting Power Evaluation Test)

Next, a disinfecting power evaluation test was performed using the acidic electrolyzed water of the example. First, 20 g of disodium dihydrogen pyrophosphate (Taihei Chemical Industrial Co., Ltd.) was added and dissolved as the acid salt of an inorganic acid in 1,000 ml of acidic electrolyzed water base material 1 to the prepare the acidic electrolyzed in Test Example 1. The pH value of the acidic electrolyzed in Test Example 1 was 3.3.

Next, a strain of fungus (*Candida albicans*) was collected and added to 5 ml of the acidic electrolyzed water in Test Example 1. Next, after ultrasonic processing for 15 minutes of the acidic electrolyzed water (5 ml) containing the fungus in Text Example 1, the water was stirred and applied to an agar medium. The agar medium was placed inside a thermostatic bath at 35° C., and cultivated for 22 days. The same treatment was applied to physiological saline and the acidic electrolyzed water base material 1 instead of the acidic electrolyzed water in Test Example 1 as controls. The results are shown in FIG. 3A through FIG. 3C.

Figure 3C:
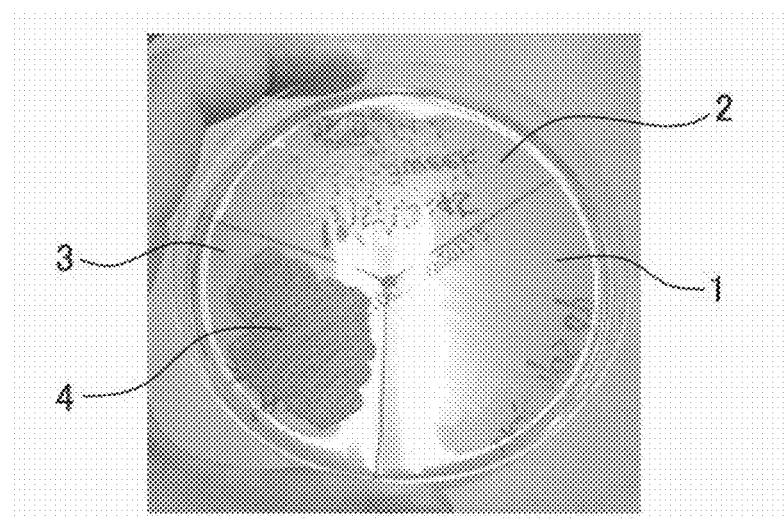
FIG. 3C is a photograph showing the disinfecting power evaluation results of the acidic electrolyzed water containing disodium dihydrogen pyrophosphate when used as the acid salt of an inorganic acid in the first example of the Present Disclosure (when the same disinfecting power test was performed after storage of the acidic electrolyzed water and the acidic electrolyzed water base material for 21 days)

FIG. 3A is a photograph showing the agar medium at the start of the test. FIG. 3B is a photograph showing the agar medium after cultivation for 24 hours using the acidic electrolyzed water immediately after preparation, the acidic electrolyzed water base material, and saline. FIG. 3C is a photograph showing agar medium when the disinfecting power test was performed after storage of the acidic electrolyzed water and the acidic electrolyzed water base material for 21 days. In FIG. 3C, physiological saline was prepared to perform a control test to confirm cultivation of the fungus. In FIG. 3A through FIG. 3C, "1" denotes the group to which the acidic electrolyzed water of Test Example 1 (acidic electrolyzed water 1 containing dissolved disodium dihydrogen pyrophosphate) has been applied ((acidic electrolyzed water+acid salt of inorganic acid) group), "2" denotes the group to which acidic electrolyzed water 1 has been applied (acidic electrolyzed water 1 group), and "3" denotes the group to which physiological saline has been applied (the physiological saline group).

In FIG. 3A, fungi 4 were not observed in any of the groups immediately after cultivation started. In FIG. 3B, fungi 4 were observed in the physiological saline group 24 hours after the start of cultivation. In FIG. 3C, fungi 4 were observed in the acidic electrolyzed water base material 1 group when tested after 21 days in storage. In contrast, no fungi 4 were observed in the acidic electrolyzed water group of the Present Disclosure under any conditions, ranging from immediately after cultivation to 22 days after the start of cultivation (see FIG. 3A, FIG. 3B, and FIG. 3C). These results confirm that the acidic electrolyzed water in Preparation Example 1 containing an acid salt of an inorganic acid (disodium dihydrogen pyrophosphate) retained its disinfecting power for a long period of time. Because the cultivation test was not performed while shielded from light, the acidic electrolyzed water of the Present Disclosure clearly was able to retain its disinfecting power even when it was not stored in a dark place.

As a negative control, 3.0 g of disodium dihydrogen pyrophosphate was dissolved in 150 ml of tap water (pH: 7.5, effective chlorine concentration: 3 ppm), and the resulting liquid (pH: 4.0) was processed in the same manner as Test Example 1. When the liquid was applied to an agar culture and cultivated in the same manner as above, fungi were observed 24 hours after the start of cultivation. It is clear from this that the disinfecting power of the acidic electrolyzed water of the Present Disclosure is not derived from the acid salt of the inorganic acid (disodium dihydrogen pyrophosphate).

4.1.5. Test Example 2 (Moisturizing Power Evaluation Test)

Next, a moisturizing power evaluation test was performed using the acidic electrolyzed water of the example. First, 8.6 g of sodium hexametaphosphate (Happou Shokai Co., Ltd.) was added and dissolved as the acid salt of an inorganic acid in 1000 ml of acidic electrolyzed water base material 2 to prepare the acidic electrolyzed in Test Example 2. The pH value of the acidic electrolyzed in Test Example 2 was 3.5. Next, a 3.9 cm×3.2 cm×1.5 cm sticky rice cake (mochi) was immersed and coated for 5 minutes in the acidic electrolyzed water (100 ml) and then allowed to stand at room temperature. The surface conditions of the sticky rice cake were then observed. As a control, the same process was performed using the acidic electrolyzed water base material (100 ml), tap water (100 ml), and alcohol (an ethanol aqueous solution) (100 ml). The results are shown in FIG. 4.

Figure 4:
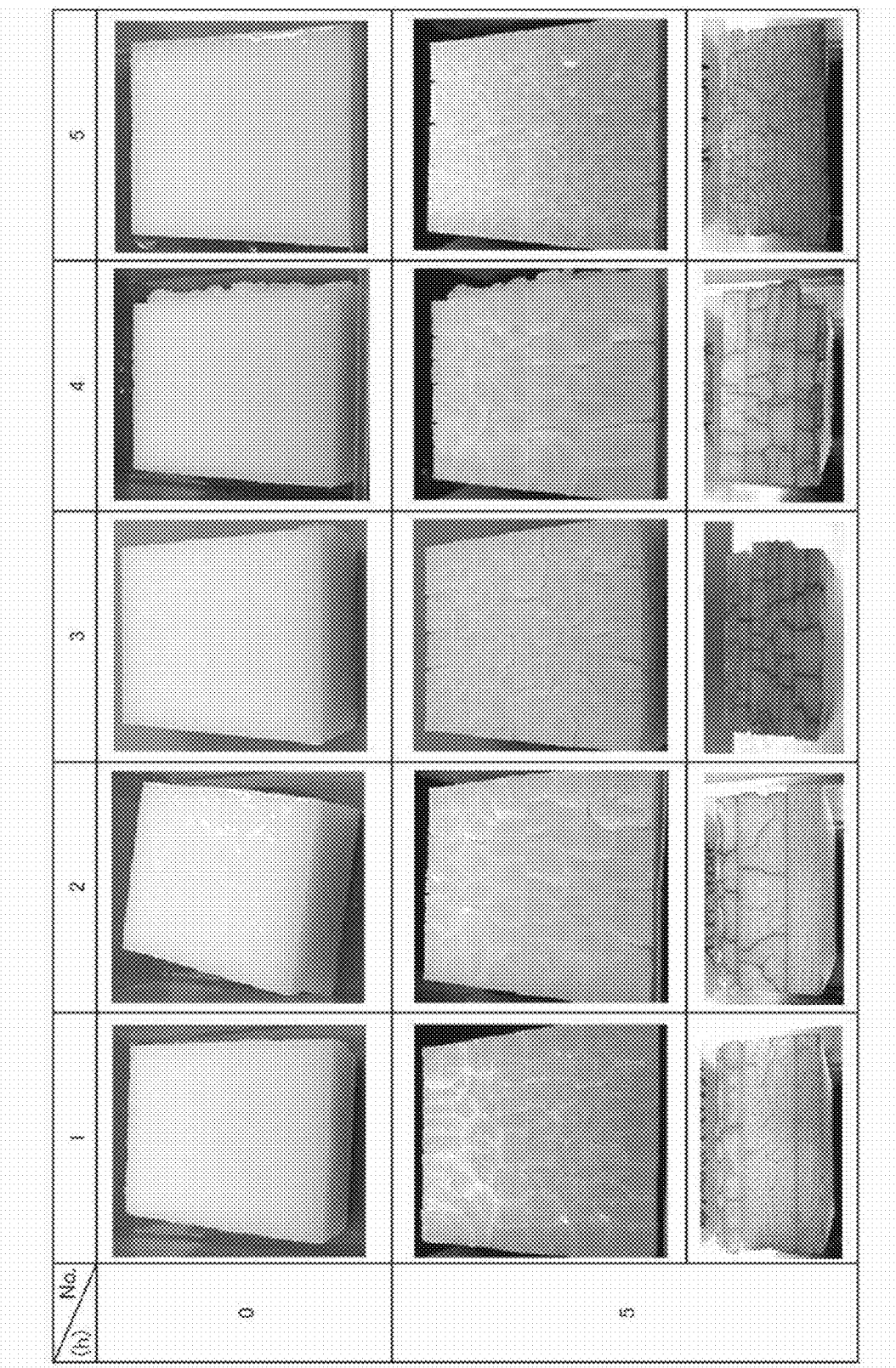
FIG. 4 shows photographs of moisturizing power evaluation results of the acidic electrolyzed water containing sodium hexametaphosphate as the acid salt of an inorganic acid in the first example of the Present Disclosure.

FIG. 4 shows photographs of moisturizing power evaluation results of the acidic electrolyzed water containing, as the acid salt of an inorganic acid, sodium hexametaphosphate in the second text example of the Present Disclosure. In FIG. 4, Test No. 1 denotes the group to which the acidic electrolyzed water of Test Example 2 (acidic electrolyzed water 1+sodium hexametaphosphate), Test No. 2 denotes the group to which acidic electrolyzed water 2 has been applied, Test No. 3 denotes the group to which nothing has been applied, Test No. 4 denotes the group to which tap water has been applied, and Test No. 5 denotes the group to which alcohol has been applied. FIG. 4 shows photographs of each group immediately after application (zero hours after application) and five hours after application. In order to make it easier to check for cracks, the surfaces of the sticky rice cakes in the photographs were stained with red ink five hours after application.

In the results, small cracks were observed two hours after application in the group to which the acidic electrolyzed water of Test Example 2 had been applied (Test No. 1). Fine cracks were observed 15 minutes after application in the group to which the alcohol had been applied (Test No. 5). Cracks were observed in the surface of the sticky rice cakes two hours after application in the case of the group to which the acidic electrolyzed water base material 2 had been applied (Test No. 2), the group to which nothing had been applied (Test No. 3), the group to which tap water had been applied (Test No. 4), and the group to which alcohol had been applied (Test No. 5). From these results, it is clear that the acidic electrolyzed water of Preparation No. 2 has moisturizing action because of the inclusion of the acid salt of an inorganic acid (sodium hexametaphosphate).

While a preferred embodiment of the Present Disclosure is shown and described, it is envisioned that those skilled in the art may devise various modifications without departing from the spirit and scope of the foregoing Description and the appended Claims.

What is claimed is:

1. A method of preparing acidic electrolyzed water, comprising:
   preparing an acidic electrolyzed water base material comprising an effective chlorine concentration equal to or greater than 15 ppm;
   adding an acid salt of an inorganic acid to the acidic electrolyzed water base material; and
   purifying the acidic electrolyzed water base by electrolyzing a chlorine-based electrolyte solution,
   wherein the acid salt of an inorganic acid is disodium dihydrogen pyrophosphate or sodium dihydrogen phosphate,
   wherein the prepared acidic electrolyzed water consists of the acidic electrolyzed water base material consisting of an effective chlorine concentration equal to or greater than 15 ppm and the acid salt of an inorganic acid.

2. The method of claim 1, wherein the acid salt of an inorganic acid is disodium dihydrogen pyrophosphate.

3. The method of claim 1, wherein the acid salt of an inorganic acid is sodium dihydrogen phosphate.

4. The acidic electrolyzed water of claim 1, wherein the LD50 value of the acid salt of the inorganic acid is greater than 300 mg.

5. The method of claim 1, wherein the pH value is equal to or greater than 3.0 and less than 7.0.

6. The method of claim 1, wherein the chlorine-based electrolyte solution comprises a solution of selected from a chloride of an alkali metal and a chloride of an alkaline-earth metal.

7. The method of claim 1, wherein the chlorine-based electrolyte solution comprises a solution of a chloride of an alkali metal selected sodium chloride and potassium chloride.

8. The method of claim 1, wherein the chlorine-based electrolyte solution comprises a sodium chloride solution.

9. The method of claim 1, wherein the chlorine-based electrolyte solution comprises a solution of a chloride of an alkaline-earth metal selected from calcium chloride or magnesium chloride.

10. A method of preparing acidic electrolyzed water, comprising:
    preparing an acidic electrolyzed water base material comprising an effective chlorine concentration equal to or greater than 15 ppm;
    adding an acid salt of an inorganic acid to the acidic electrolyzed water base material; and
    purifying the acidic electrolyzed water base by electrolyzing a chlorine-based electrolyte solution,
    wherein the acid salt of an inorganic acid is selected from disodium dihydrogen pyrophosphate, sodium hexametaphosphate, and sodium dihydrogen phosphate,
    wherein the $LD_{50}$ value of the acid salt of the inorganic acid is greater than 300 mg, and
    wherein the pH value is equal to or greater than 3.0 and less than 7.0,
    wherein the prepared acidic electrolyzed water consists of the acidic electrolyzed water base material consisting of an effective chlorine concentration equal to or greater than 15 ppm, the acid salt of an inorganic acid, and having a pH value equal to or greater than 3.0 and less than 7.0.

* * * * *